US006576474B2

(12) United States Patent
Wallach

(10) Patent No.: US 6,576,474 B2
(45) Date of Patent: Jun. 10, 2003

(54) APPARATUS AND METHOD OF MONITORING AN ANALYTE

(75) Inventor: Donald F. H. Wallach, Geneva (CH)

(73) Assignee: GroupTek, Inc., Andover, MA (US)

( * ) Notice: Subject to any disclaimer, the term of this patent is extended or adjusted under 35 U.S.C. 154(b) by 0 days.

(21) Appl. No.: 10/211,293

(22) Filed: Aug. 5, 2002

(65) Prior Publication Data

US 2003/0003593 A1 Jan. 2, 2003

Related U.S. Application Data

(62) Division of application No. 09/774,242, filed on Jan. 31, 2001, now Pat. No. 6,428,748.

(51) Int. Cl.⁷ .............................. G01N 21/77
(52) U.S. Cl. .................... 436/169; 422/56; 422/57; 436/2; 436/164
(58) Field of Search ............... 422/56, 55, 57, 422/61, 68.1, 82.05; 436/2, 164, 166, 169, 172

(56) References Cited

U.S. PATENT DOCUMENTS

| | | |
|---|---|---|
| 2,485,556 A | 10/1949 | Clark |
| 3,067,015 A | 12/1962 | Lawdermilt |
| 3,520,124 A | 7/1970 | Myers |
| 4,003,709 A | 1/1977 | Eaton et al. |
| 4,066,403 A | 1/1978 | Bruschi |
| 4,098,577 A | 7/1978 | Halpern |
| 4,105,800 A | 8/1978 | Jahns et al. |
| 4,154,107 A | 5/1979 | Giezen et al. |
| 4,195,056 A | 3/1980 | Patel |
| 4,195,058 A | 3/1980 | Patel |
| 4,212,153 A | 7/1980 | Kydonieus et al. |

(List continued on next page.)

FOREIGN PATENT DOCUMENTS

| | | |
|---|---|---|
| CA | 2184677 A | 5/1998 |
| FR | 2735705 | 12/1996 |
| JP | 5321147 | 12/1993 |

OTHER PUBLICATIONS

Bell, C. et al., "Disposable oxygen electrode system without membranes applied to the detection of ultrahigh–temperature milk spoilage", Netherlands Milk and Diary Journal, vol. 49 pp. 139–149 (1995).

Chang, George et al., "Trimethylamine–specific electrode for fish quality control", Journal of Food Science, vol. 41 pp. 723–724 (1976).

Essary, E.O. and Halpin, B., Influence of Cooking and Storage Conditions on pH and Hydrogen Sulfide Production in Hard Cooked Eggs, 70$^{th}$ Annual Meeting of the Poultry Sciences Assoc., vol. 60, No. 7. p. 1654 (1981).

Germs, A.C., "Hydrogen Sulphide Production in Eggs and Egg Products as a Result of Heating," J. Sci. Fd Agric., vol. 24, pp. 7–16 (1973).

Gyosheva, H. et al., "Compounds forming the aroma complex of Bulgarian sour milk", Milchwissenschaft, vol. 37, No. 5, pp. 267–269 (1982).

Hajizadeh, K. et al., "Immobilization of lactate oxidase in a poly (vinyl alcohol) matrix on platinized graphite electrodes by chemical cross–linking with isocyanate", Talanta, vol. 38, No. 1, pp. 37–47 (1991).

(List continued on next page.)

Primary Examiner—Jill Warden
Assistant Examiner—Sam P. Siefke
(74) Attorney, Agent, or Firm—Fish & Richardson P.C.

(57) ABSTRACT

A detector for monitoring an analyte includes an analyte-sensing composition. The analyte-sensing composition has a visible color intensity or emission intensity (e.g., fluorescence intensity) that changes as the analyte concentration contacting the detector changes. The intensity changes can be visible to the human eye, or identified by an instrument. The analyte can include carbon dioxide, a volatile amine or a volatile carboxylic acid.

6 Claims, 5 Drawing Sheets

U.S. PATENT DOCUMENTS

| | | | |
|---|---|---|---|
| 4,285,697 | A | 8/1981 | Neary |
| 4,292,916 | A | 10/1981 | Bradley et al. |
| 4,938,389 | A | 7/1990 | Rossi et al. |
| 5,045,283 | A | 9/1991 | Patel |
| 5,053,339 | A | 10/1991 | Patel |
| 5,058,088 | A | 10/1991 | Haas et al. |
| 5,085,802 | A | 2/1992 | Jalinski |
| 5,096,813 | A | 3/1992 | Krumhar et al. |
| 5,156,780 | A | 10/1992 | Kenigsberg et al. |
| 5,180,598 | A | 1/1993 | Jozefowicz |
| 5,182,212 | A | 1/1993 | Jalinski |
| 5,254,473 | A | 10/1993 | Patel |
| 5,306,466 | A | 4/1994 | Goldsmith |
| 5,407,829 | A | 4/1995 | Wolfbeis et al. |
| 5,439,648 | A | 8/1995 | Balderson et al. |
| 5,443,987 | A | 8/1995 | DiCicco et al. |
| 5,653,941 | A | 8/1997 | Veretto et al. |
| 5,663,072 | A | 9/1997 | Honeybourne |
| 5,753,285 | A | 5/1998 | Horan |
| 5,876,753 | A | 3/1999 | Timmons et al. |
| 5,981,614 | A | 11/1999 | Adiletta |
| 6,057,162 | A | 5/2000 | Rounbehler et al. |
| 6,428,748 | B1 * | 1/2001 | Wallach .................... 422/56 |

OTHER PUBLICATIONS

Hajizadeh, K. et al., "Gamma–irradiation immobilization of lactate oxidase in poly (vinyl alcohol) on platinized graphite electrodes", Analytica Chimica Acta., vol. 243 pp. 23–32 (1991).

Park, D. et al., "Rapid Facile Solid–Phase Immunobead Assay for Screening Ciguatoxic Fish in the market place", Bull. Soc. Path. Ex., vol. 85, pp. 504–507 (1992).

Y. Blixt and E. Borch, "Using an electronic nose for determining the spoilage of vacuum–packaged beef", International Journal of Food Microbiology, 46, pp. 123–134 (1999).

Intarapichet, K. and Bailey, M. E., "Volatile Compounds Produced by Meat Pseudomonas Grown on Beef at Refrigeration Temperatures," ASEAN Food Journal, 8:14–21. (1993).

P. DeLassus, in the Kirk–Othmer Encyclopedia of Chemistry, $4^{th}$ Edition, vol. 3, John Wiley and Sons, pp. 931–962 (1995).

Israel Cabasso, in the Encyclopedia of Polymer Science and Engineering, Edition 2, vol. 9, John Wiley and Sons, p. 509–579 (1986).

Mujais, S.K. and Ivanovitch, P., Membranes for Extracorporeal Therapy, in "Replacement of Renal Function by Dialysis", John F. Maher, Editor, Kluwer Academic Publishers, Boston, pp. 181–188 (1989).

Henderson, L.W., Biophysics of Ultrafiltration and Hemofiltration, in "Replacement of Renal Function by Dialysis", Third Edition, John F. Maher, Editor, Kluwer Academic Publishers, Boston, pp. 300–326 (1989).

Samtleben, W. and Gurland, H. J., Plasma Exchange: Principles and Practice in "Replacement of Renal Function by Dialysis", Third Edition, John F. Maher, Editor, Kluwer Academic Publishers, Boston, 460–474 (1989).

Sargent, J. A. and Gotch, Frank A., Principles and Biophysics of Dialysis, in "Replacement of Renal Function by Dialysis", Third Edition, John W. Maher. Editor, Kluwer Academic Publishers, Boston, pp. 87–143 (1989).

Labuda, T. P. and Fu, B., "Use of Time/Temperature Integrators, Predictive Microbiology, and Related Technologies for Assessing the Extent and Impact of Temperature Abuse on Meat and Poultry Products," Journal of Food Safety vol. 15, No. 3, pp. 201–227 (1995).

Wells, J. H. and Singh, R. P, "The Application of Time–Temperature Technology to Food Quality Monitoring and Perishable Inventory Management", in Mathematical Modeling of Food Processing Operations, S. Thorne, Editor; Elsevier Applied Sciences, London, pp. 271–344 (1992).

Edsall, J. T. and Wyman, J. "Carbon Dioxide and Carbonic Acid", in Biophysical Chemistry, vol. 1, Academic Press, New York, pp. 550–590 (1958).

Dawson, R. M. C., et al, "The Standardization and Measurement of pH", in Data for Biochemical Research, Clarendon Press, Oxford; pp. 418–448, (1986).

Luong, J. H. T. et al, "Applications of Polarography for Assessment of Fish Freshness," Journal of Food Science, vol. 56, No. 2, pp. 335–337 (1991).

Schooner, F. et al, "Colorimetric Assay for Free Fatty Acids in Butter Using Flow–Injection and Immobilized Enzymes," Journal of Food Science, vol. 56, pp. 1229–1232 (1991).

G. L. Witucki, "A Silane Primer: Chemistry and Applications of Akoxy Silanes," Journal of Coatings. Technology, vol. 65, No. 82, pp. 57–61 (1993).

Tokatli, K. and Öziglen, M., "Temperature Effects on Permeation of Modified Atmospheric Gas Mixtures Through a Low–Density Polyethylene Film," Polymer International, vol. 30, No. 1, pp. 109–113 (1993).

Krenik, K. D. et al, "Comparison of anti–fading reagents used in immunofluorescence," Journal of Immunological Methods, vol. 117, No. 1, pp. 91–97 (1989).

Longin, A. et al, "Comparison of Anti–fading Agents Used in Fluorescence Microscopy: Image Analysis and Laser Confocal Microscopy Study," Journal of Histochemistry and Cytochemistry, vol. 41, No. 12, pp. 1833–1840 (1993).

Wallach, D.F.H. et al, "Preparation and Properties of 3,6 Dihydroxy–2,4–bis–[N, N'–di–(carboxymethyl)–aminomethyl]fluoran," Analytical Chemistry, vol. 31, pp. 456–460 (1959).

Wallach, D.F.H., and Steck, T., "Fluorescence Techniques in the Microdetermination of Metals in Biological Materials," Analytical Chemistry, 35, pp. 1035–1044 (1963).

Wallach, D.F.H., and Steck, T. "Fluorescence Techniques in the Microdetermination of Metals in Biological Materials. II. An Improved Method for Direct Complexometric Titration of Calcium in Small Serum Samples," Analytical Biochemistry, vol. 6, pp. 176–180 (1963).

Munder, P. et al, "Cell Propagation on Films of Polymeric Fluorocarbon as a Means to Regulate Pericellular pH and $pO_2$ in Culture Monolayers," FEBS Letters, vol. 15, pp. 191–196 1971.

Jensen, M, et al, "Comparative Growth Characteristics of VERO Cells on Gas–Permeable and Conventional Supports," Experimental Cell Research, vol. 84, pp. 271–281 (1974).

Giannuzzi, L. et al, "Influence of packaging film permeability and residual sulphur dioxide on the quality of pre–peeled potatoes," International Journal of Food Science & Technology, 23, pp. 147–152 (1988).

Shimoda, M. et al, "Behavior of Diffusion, Permeation and Sorption of Flavor Compounds in Vapor Phase with Polyethylene Film," Nippon Shokuhin Kogyo Gakkaishi, vol. 34, No. 6, pp. 402–406 (1987).

* cited by examiner

APPARATUS AND METHOD OF MONITORING AN ANALYTE

PRIORITY STATEMENT

This application is a divisional of U.S. application Ser. No. 09/774,242, filed Jan. 31, 2001, now U.S. Pat. No. 6,428,748 issued Aug. 6, 2002 incorporated by reference in its entirety.

TECHNICAL FIELD

This invention relates to an apparatus and method for monitoring an analyte.

BACKGROUND

Volatile compounds generated during food spoilage have conventionally been monitored by standard chemical laboratory methods. Volatile biological metabolites can be monitored to diagnose disease using similar methods. Assays have been developed to monitor the volatile compounds with improved accuracy, speed, sensitivity, selectivity and reduced cost. Some approaches to monitoring the compounds include electronic sensors, qualitative visual sensors, or analytical techniques such as gas-liquid chromatography.

Other approaches to protecting consumers from spoiled food rely on the appearance of spoilage molecules after passage of a predictable amount of time. For example, "expiration dates" stamped on food containers, such as milk or juice containers, give consumers and indication of when spoilage might occur. The accuracy of the stamped dates depends on the history of conditions the food product is exposed to before consumption and is not dependable after the container is opened.

Another method of monitoring the potential quality of refrigerated, controlled-atmosphere-packaged and deep-frozen foods includes time temperature indicators, which monitor and indicate a possible unfavorable temperature history of refrigerated food. This approach typically does not provide specific information about the chemicals generated by the food product. Most consumer products rely on the combination of time stamps, food appearance, odor, and color to avoid spoilage.

SUMMARY

A detector for monitoring an analyte includes an analyte-sensing composition. The analyte-sensing composition has a visible color intensity or emission intensity (e.g., fluorescence intensity) that changes as the analyte concentration contacting the detector changes. The intensity changes can be visible to the human eye, or identified by an instrument. The analyte can include carbon dioxide, a volatile amine or a volatile carboxylic acid.

In one aspect, a detector for monitoring a sample for the presence of an analyte includes a carrier, an analyte-sensing composition, a hydrophobic barrier, and an outer barrier. The carrier can be porous or fibrous. The analyte-sensing composition includes an indicator dye, a buffer, and an osmotic control agent and is contained by the carrier. The indicator dye can include an emissive dye, such as fluorescein complexon, or a colored dye, such as a phthalic acid derivative. The phthalic acid derivative can include o-cresolphthalein, phenolphthalein, or thymolphthalein. The hydrophobic barrier is on one surface of the carrier and is arranged to contact a test material. The hydrophobic barrier can include a hydrophobic silane coating, a fluorocarbon coating, or a laminated hydrophobic sheet. The outer barrier covers a surface of the carrier opposite the outer barrier. The outer barrier can be impermeable to water and gases. In certain implementations, the outer barrier can be transparent to visible light.

In another aspect, a method of detecting an analyte includes contacting the detector with a food product, body fluid or tissue and monitoring the detector for a change in visible color intensity or emission intensity from the indicator dye, which indicates the presence of the analyte. Monitoring can include detecting the change with an instrument or the human eye. The presence of the analyte can change the pH within the carrier. The method can include removing the detector from a sealed package prior to contacting the food product, body fluid or tissue.

In another aspect, a method of manufacturing a detector includes depositing a solution containing a solvent and the analyte-sensing composition on a carrier, removing the solvent, forming a hydrophobic barrier on a surface of the carrier; and placing an outer barrier on a surface of the carrier opposite the outer barrier.

In certain implementations, the detector can include a permeation modulator covering a portion of the hydrophobic barrier. The permeation modulator can have a lower permeability than hydrophobic layer or the carrier. The detector can be a portion of a food package or a hygiene product.

The details of the detector are set forth in the accompanying drawings and the description below. Other features, objects, and advantages will be apparent from the description and drawings, and from the claims.

DETAILED DESCRIPTION

Figure 1:
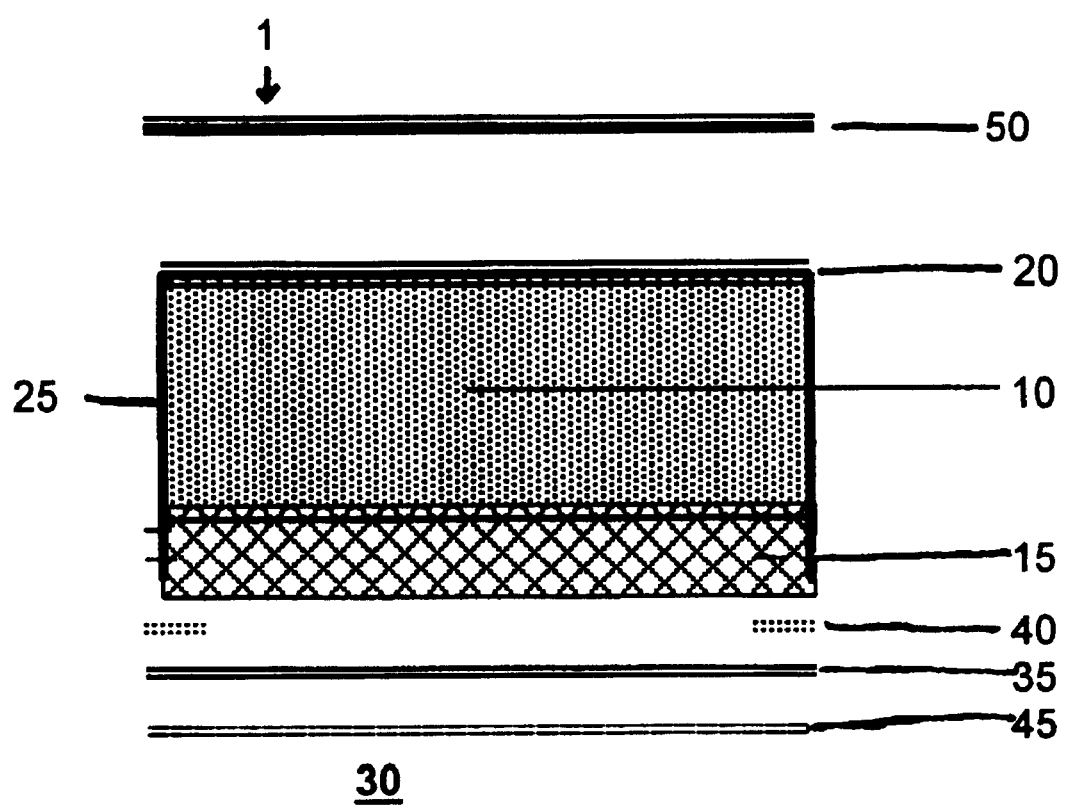
FIG. 1 is a cross-sectional drawing depicting a detector.

The detector is configured to monitor a sample for the presence of an analyte by changes in emission intensity or visible color intensity. The intensity changes can be visible to the human eye, or identified by an instrument. The analyte can include carbon dioxide, a volatile amine or a volatile carboxylic acid. The analyte can be a compound used in food packaging, or a metabolite generated during food spoilage or health-related processes, such as phagocytic activity. The detector can monitor for the presence of the analyte in food packaging, including controlled atmosphere packaging, time-temperature applications, or medical diagnostic applications.

A list of analyte compounds is produced in Table 1.

TABLE 1

| Compound | Molecular Weight (g/mol) | Melting point (° C.) | pK | Common source |
|---|---|---|---|---|
| Ammonia | 17 | −78 | 9.25 | Urine |
| Methylamine[1] | 31.1 | −93.5 | 10.79 | Seafood spoilage |
| Carbon dioxide[2] | 44 | −78.5 | 6.35 10.33 | Blood gas; aerobic bacteria |
| Trimethylamine | 59.1 | −124 | 9.91 | Seafood spoilage |
| Acetic acid | 60.1 | −121 | 4.76 | Yeast/bacterial metabolism |
| Proprionic acid | 74.1 | −21 | 4.87 | Dairy product bacterial metabolism |
| Butyric acid | 88.1 | −5 | 4.82 | Dairy product bacterial metabolism |
| Isobutyric acid | 88.1 | −47 | 4.6 | Dairy product bacterial metabolism |
| Putrescine | 88.2 | 27–28 | 9.35 10.80 | Meat spoilage |
| 2,3-Butanedione[3] | 89.0 | 26 | | Meat, butter |
| Lactic acid | 90.1 | 28–33 | 3.73 | Dairy product bacterial metabolism |
| Valeric acid | 102.1 | −33.8 | 4.81 | Dairy product bacterial metabolism |
| Isovaleric acid | 102.1 | −37.6 | 4.78 | Dairy product bacterial metabolism |
| Cadaverine | 102.2 | 9 | 10.05 10.93 | Meat spoilage |
| Caproic acid | 116.16 | −3 | 4.78 | Dairy product bacterial metabolism |

[1]Methyl sulfide (M. Wt. 62.13 g/mol, M. P. - 98° C.) and dimethyl sulfide (M. Wt. 94.2 g/mol, M.P. - 85° C.) are methyl/dimethyl amine derivatives (related to meat/sea food spoilage) can also be generated.
[2]Also used in controlled atmosphere packaging.
[3]Also known as diacetyl.

Carbon dioxide present in pure water or aqueous salt solution is partially hydrated to carbonic acid, $H_2CO_3$. The acidity of water containing the dissolved gas arises from dissociation of $H_2CO_3$ to bicarbonate ($HCO_3^-$) and $H^+$ and dissociation of $HCO^-_3$ to carbonate ($CO_3^{2-}$) and $H^+$ under alkaline conditions. The hydration reaction is relatively slow and involves large activation energy. Therefore, more than 99% of dissolved carbon dioxide in media not containing bases is present as the gas. For this reason the first ionization constant for the conversion of $CO_2$ to $HCO_3^-$ and $H^+$ is about 50–500 times smaller than the pKs for most other volatile carboxylic acids listed in Table 1. Bicarbonate is a very weak acid and dissociation to carbonate takes place only at alkaline pH. In pure water or aqueous sodium chloride solution, the solubility of $CO_2$, $qCO_2$, equals ($CO_2$+ $H_2CO_3$). The solubility of $CO_2$ in 0.02 N NaCl decreases with temperature, as shown in Table 2.

TABLE 2

| $pCO_2$ (atmosphere) | $qCO_2$ at 10 ° C. (mol/l) | $qCO_2$ at 25 ° C. (mol/l) |
|---|---|---|
| 1.000 | 0.0610 | 0.0328 |
| 0.800 | 0.0488 | 0.0262 |
| 0.600 | 0.0366 | 0.0366 |
| 0.400 | 0.0244 | 0.0195 |
| 0.250 | 0.0153 | 0.0092 |
| 0.200 | 0.0122 | 0.0049 |
| 0.150 | 0.0092 | 0.0023 |
| 0.100 | 0.0061 | 0.0012 |
| 0.050 | 0.0031 | 0.0005 |

Carbon dioxide can be formed by microbes. Because carbon dioxide is not an end product of anaerobic metabolism, absence of carbon dioxide does not assure absence of anaerobic bacteria. By monitoring for other volatile amines and volatile carboxylic acids that can be generated by microbes, the sensor can more effectively monitor food spoilage. For example, volatile amines can be monitored to assess fish or seafood freshness and volatile carboxylic acids can be monitored to assess dairy freshness. Alternatively, carbon dioxide can be added to food product packaging to control the atmosphere of the packaging.

Figure 2:
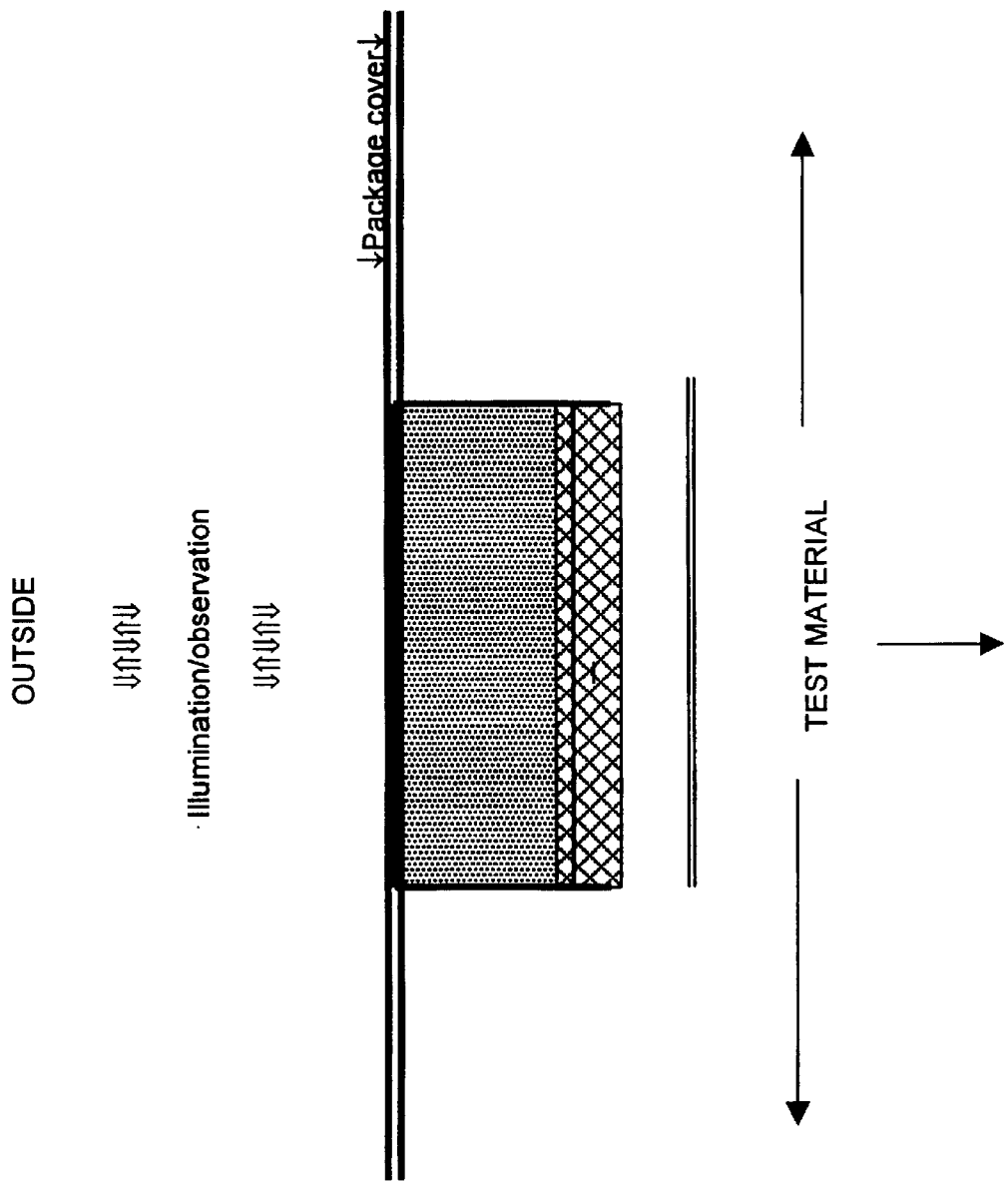
FIG. 2 is a cross-sectional drawing depicting a detector on the inside of a compartment.
Figure 3:
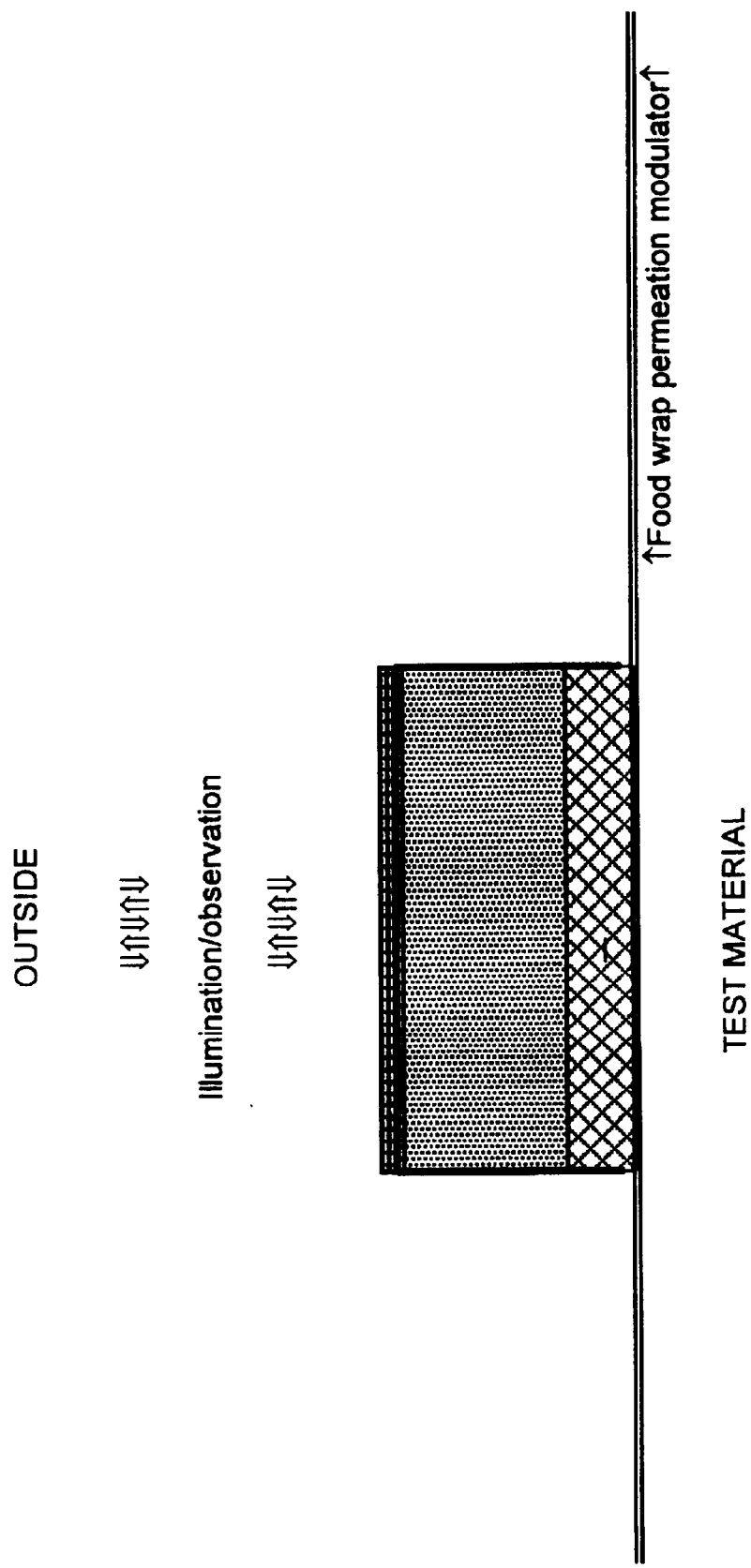
FIG. 3 is a cross-sectional drawing depicting a detector adhered to the outside of a package.
Figure 4:
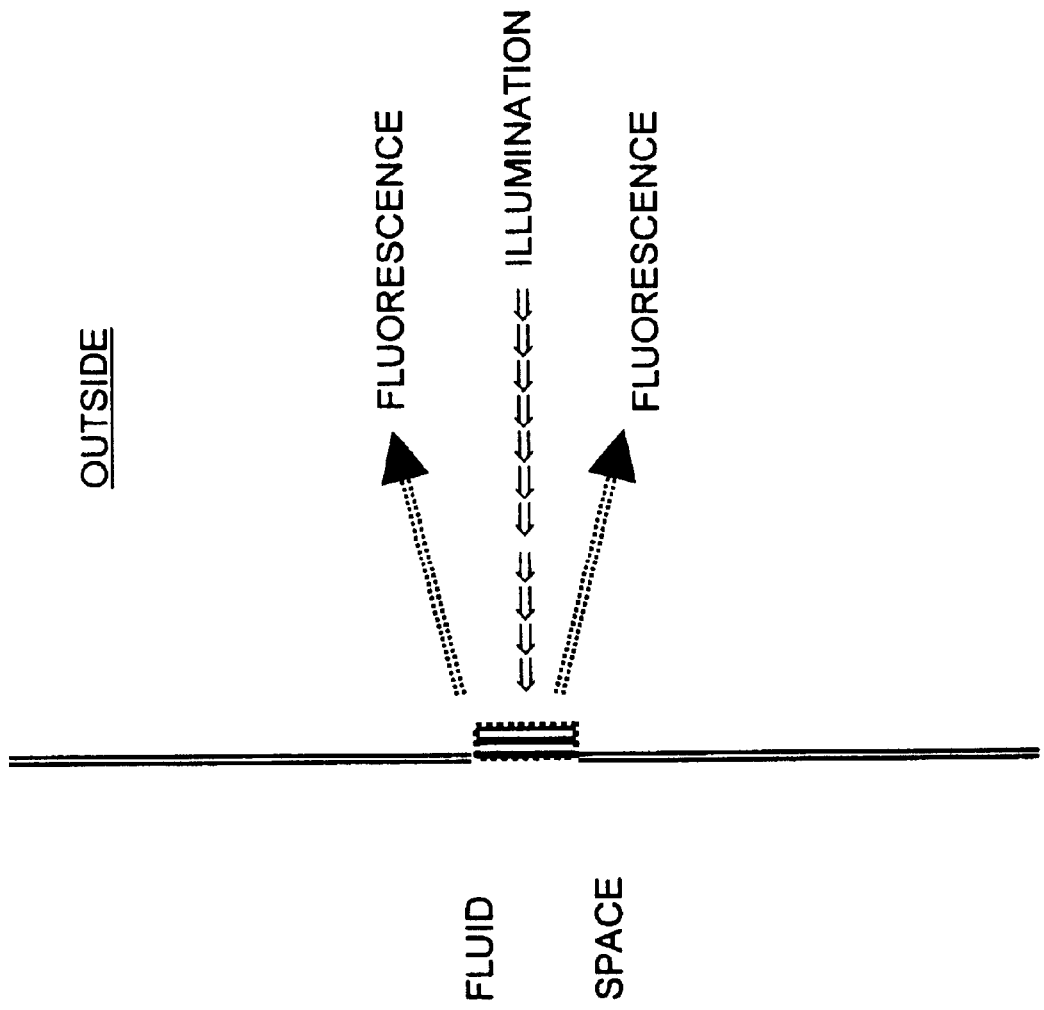
FIG. 4 is a cross-sectional drawing depicting a detector arranged in a wall of a container.
Figure 5:
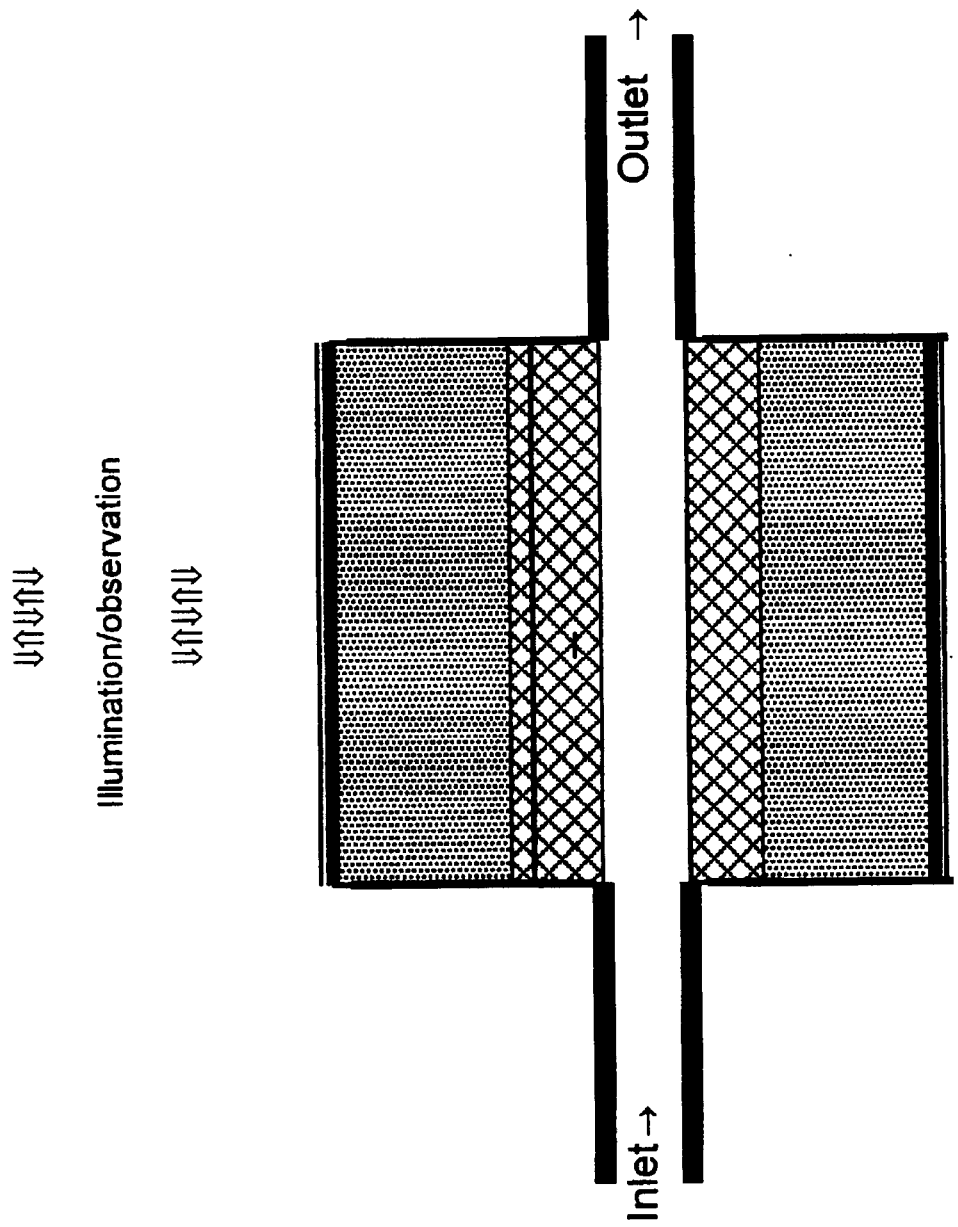
FIG. 5 is a cross-sectional drawing depicting a detector in tubular form.

The detector is a multi-layered array containing an analyte-sensing composition. The detector can be formed into a planar structure as shown in FIG. 1. The outer layer of the detector can be configured to allow use of the detector on the inside of a compartment sealed within a gas-impermeable package or in a bottle cap as depicted in FIG. 2. The planar structure can be incorporated in, for example, a label adhered to the outside of a package wrapped in common, gas-permeable food wrap as shown in FIG. 3. The detector can be arranged in a wall of a container, as shown in FIG. 4 or in a tubular form for continuous monitoring of gases, blood, carbonation lines, and other flowing fluids as shown in FIG. 5. The detectors can be incorporated into packaging for liquid foods. For example, the detector can be incorporated into snap-top plastic containers for fresh and processed liquid foods, screw-cap plastic containers for fresh and processed liquid foods, screw-cap bottles for carbonated beverages, screw-cap-spout paper-composite containers, seals for screw-cap-spout paper-composite containers, windows for paper-composite containers, and seals for spouts for tetrapak-type paper-foil composite containers.

Referring to FIG. 1, the detector 1 includes a carrier 10, which contains the analyte-sensing composition. The carrier 10 contacts an inner hydrophobic barrier 15 and an outer barrier 20. The peripheral border of the detector is sealed by seal 25, eliminating edge contamination within the detector. The hydrophobic layer 15 is exposed to a test material 30. Test material 30, such as a food, a body fluid, or a tissue, is tested for the presence of an analyte. The permeation surface area of the detector can be from 9 to 256 $mm^2$, or from 25 to 225 $mm^2$, for example, 100 $mm^2$. The edge area of the detector can be 8 $mm^2$. The detector can have a diameter from 5 mm to 10 mm.

The carrier 10 can be a porous sheet having a thickness of less than 0.5 mm, or less than 0.3 mm. The carrier contains the analyte-sensing composition and allows access of water vapor and other volatile materials to the analyte-sensing composition. The carrier can be impregnated with the analyte-sensing composition. The carrier allows the sensing composition to be observed visually or photometrically. For example, the carrier can provide a bright, white background, which can enhance observation. The carrier can be manufactured from a material that is non-reactive with the analyte-sensing composition and can have a minimal fixed charge or acid residue. Suitable carriers can include, for example, from analytical paper, such as Whatman, Grades 1 or 41, or Schleicher and Schuell 22, 590, and 240a,b, 243a,b, cellulose paper, hydrophilic nylons, glass fibers or cellulose esters. Non-fluorescent, inert carriers that are brightened with high purity titanium dioxide can be useful for monitoring the detector by fluorescence measurements. The carrier materials can be treated and processed for use in the detector.

The inner face of the carrier 10 contacts hydrophobic barrier 15. Carrier 10 can be impregnated with a hydrophobic material or has an adsorbed hydrophobic layer to form hydrophobic barrier 15. The hydrophobic barrier 15 can reduce or eliminate access of water or materials dissolved in water to the carrier and the analyte-sensing composition. The hydrophobic barrier 15 can prevent contamination of the analyte-sensing composition by components of the test material 30 while concurrently allowing rapid access of the analyte to the analyte-sensing composition.

The hydrophobic barrier 15 can be rendered hydrophobic by silanization of the inner surface of the carrier 10 or by coating carrier 10 with an appropriate fluorocarbon. Methods of forming a surface suitable for use as a hydrophobic barrier are described, for example, in G. L. Witucki, "A silane primer: chemistry and applications of alkoxysilanes", J. Coatings. Technol. 65:57–61 (1993); S. Owaki and K. Yamada Japanese Patent 5321147/93321147 (1993); J. Croquelois French Patent 2,735,705; J. G. Adiletta U.S. Pat. No. 5,981,614; or Y. T. Kenigsberg and E. Schori U.S. Pat. No. 5,156,780, each of which is incorporated by reference in its entirety. Commercially available silylating agents, such as alkoxysilanes, for example, (methyl 3-trimethylsilyloxy) crotonate, SIGMACOTE® (a mixture of chlorotrialkylsilanes) and "Bind Silane" (3-trimethoxysilyl) propyl methacrylate), are widely used laboratory silylation reagents that can rapidly silylate hydroxyl groups such as the secondary hydroxyl groups that abound in cellulose. Another general approach to forming the hydrophobic barrier can include plasma treatment of the carrier surface which can allow greater control of hydrophobic layer thickness, as described, for example, in U.S. Pat. No. 5,876,753, which is incorporated by reference in its entirety. The hydrophobic barrier 15 can also be prepared by lamination of a hydrophobic non-woven sheet, or a hydrophobic microporous filter sheet on the internal surface of the carrier.

The outer barrier 20 is attached to a surface of carrier 10 opposite hydrophobic layer 15. Outer barrier 20 seals the carrier layer 10, and the analyte-sensing composition, from exposure to the external environment. Outer barrier 20 can be impermeable to water and gases and can be transparent to visible light for visual or photometric observation of the analyte-sensing composition emission or visible color. The outer barrier 20 can be opaque to ultraviolet light to protect the test material 30 from degradation. Outer barrier 20 can include a thermoplastic polyester, for example a non-UV transmitting thermoplastic, a polycarbonate or polycarbonate blend, or a high-density polyethylene.

Analyte permeation through the hydrophobic layer into the carrier can be modulated by a permeation modulator 35. For example, penetration of any of the analytes listed in Table 1 into the carrier 10 and the analyte-sensing composition can be rapid, and the resulting response time of the detector will be fast. The fast detector response can be too fast for certain time specific or time-temperature specific applications in which the analyte does not build up instantaneously. In these applications, it can be advantageous to monitor increases in analyte concentration over time. For such applications, the optional permeation modulator 35 is positioned between the test material 30 and the detector 1. In certain implementations, permeation modulator 35 can include a layer that can be optionally perforated to avoid contaminating the detector with lipids or other contaminants that may associate with the hydrophilic layer 15.

The hydrophobic layer 15 can be attached to permeation modulator 35 by an adhesive 40. The permeation modulator 35 can be a layer permeable to water vapor and gases, but not permeable to liquid water, and has a lower permeability than the hydrophobic layer or the carrier of the detector. The permeation modulator can include polyethylene or polyvinylidene chloride. The permeation modulator can have a thickness between 0.001 and 5 mm, or between 0.01 and 1 mm. For example, detector 1 can be attached to a food wrap film as a label.

The permeation modulator can hinder permeation of the analyte, thereby delaying the response of the detector to the analyte. Permeation can follow the equation $Q=Pat(pGas_e-pGas_i)/x$, where Q is the flux of gas in mols, P is the permeability coefficient for a specified gas and membrane at a specified temperature (mols.cm/cm$^2$.sec.atmosphere), a is the surface area for permeation (cm$^2$), t is the time (seconds), $pGas_e$ and $pGas_i$ are the partial pressures (atmospheres) at external or internal membrane surfaces, respectively, and x is the membrane thickness (cm). For 1 mol gas passing in 1 sec across a 1 cm-thick, 1 cm$^2$ zone with a partial pressure differential of one atmosphere, Q=P. For a given pressure differential and time, the rate of transfer is reduced by the resistance given by P, the area available for permeation and the membrane thickness. When values of P are very small, $(pGas_e-pGas_i)$ will approximate $pGas_e$ except when t is large. The permeation of carbon dioxide through low-density polyethylene follows the Arrhenius expression between −16 to 40° C., with an activation energy of 8.4–9 kcal/mol. See T. Tokatli, and M. Oziglen, "Temperature effects on permeation of modified atmospheric gas mixtures through a low-density polyethylene film", Polymer Intl. 30:109–113 (1993). The P values, for carbon dioxide at 25° C. ranges from $2\times10^{-11}$–$6\times10^{-13}$ for plasticized polyvinylidene chloride to $1\times10^{-12}$ for high-density polyethylene to $5\times10^{-12}$ for low-density polyethylene. See Modern Plastics Encyclopedia, 1995, 56–81, 595. With the exception of ammonia, methylamine and trimethylamine, the permeations of the analytes listed in Table 1 are lower than that of carbon dioxide.

The detector 1 can include an inner backing layer 45 between the test material 30 and the hydrophobic layer 15 to prevent contamination of the chemistry layer after manufacture. Inner backing layer 45 is impermeable to analytes and provides a gas-tight seal prior to use. Removal of the inner backing layer starts the detection period. An outer backing layer 50 in contact with the outer barrier 20 can protect the detector during manufacture, transport and storage. When the analyte-sensing composition includes a fluorescent material, the inner and outer backing layers can be opaque to reduce or prevent photobleaching of the fluorescent material. The backing can be a self-peeling backing.

The analyte-sensing composition contained within the carrier responds to changes in concentration of the analyte in the test material. Specifically, the analyte-sensing composition responds to changes in concentration of carbon dioxide, volatile carboxylic acids or volatile amines, such as those listed in Table 1.

The analyte-sensing composition includes an indicator dye, such as a fluorescent dye, a buffer, and an osmotic control agent. The analyte-sensing composition is applied to the carrier as, for example, an aqueous solution. After impregnating into the carrier, for example by applying a calibrated stamp to the carrier, the analyte-sensing composition is dried. Osmolarity of the analyte-sensing composition can be between 0.005 and 0.015 osM. The osmolarity largely arises from the presence of the buffer. Because the hydrophobic barrier 15 is permeable to water vapor, water can move into and out of the carrier until the water activity within the detector and external to the detector is identical. However, the osmolarity of many test materials, including food, tissue and body fluids, is near 0.3 osM. As a result, the test materials can tend to extract water from the detector, altering the sensitivity of the detector. An osmotic control agent, such as low molecular weight alcohols including glycerol, propylene glycol or sorbitol or other compounds that will not permeate the hydrophobic barrier, can be used to raise the osmolarity within the carrier. The addition of the osmotic control agent can increase the osmolarity of within the detector to 0.25 to 0.5 osM, which is hyperosmolar to the test material. A liquid osmotic control agent, such as glycerol or propylene glycol, can facilitate manufacture of the detector.

In some certain implementations, a stable, non-toxic anti-fading reagent, such as n-propyl gallate, 1,4-diazobiscyclo(2,2,2-octane) or ascorbic acid can be included in the analyte-sensing composition. Examples of anti-fading reagents are described, for example, in K. D Krenik et al. J. Immunol. Methods, 117, 91–97 (1989) and A. Longier et al. J. Histochem. & Cytochem. 41:1833–1840 (1993).

The indicator dye can be an emissive indicator, such as a fluorescent dye, or a colored dye. One suitable fluorescence dye is fluorescein complexon. Fluorescein complexon can be readily monitored visually under most lighting conditions and can be monitored easily using instrumental techniques. Fluorescein complexon has a molecular weight of 622 g/mol and has the formula bis(N,N-bis(carboxy-methyl)-aminomethyl)fluorescein. Fluorescein complexon is described, for example, in D. F. H. Wallach et al. Anal. Chem. 31:456–460 (1959) and D. F. H. Wallach and T. Steck Anal. Chem. 35:1035–1044 (1963), each of which is incorporated by reference in its entirety.

Fluorescein complexon can also be called fluorexon or calcein. Fluorescein complexon is a (methylimino) diacetate derivative of fluorescein and is related to the (methylimino) diacetate derivative of a number of dyes, including calcein acetoxymethyl ester, cresolphthalein complexon, thymolphthalein complexon, umbelliferone complexon and xanthon complexon. While these molecules shares some acid-base characteristics and metal-binding with fluorescein complexon, fluorescein complexon can form detectors that perform more reliably and accurately than similar detectors prepared with these other dyes. Fluorescein complexon (CAS#14161-15-0) has no known toxicity is inexpensive, is commercially available and is used in certain ophthalmic preparations (Natl. Formulary 36:96).

Certain properties of fluorescein complexon are summarized in Table 4.

TABLE 4

| | pH ~ 2* | pH ~ 7 | pH ~ 9 | pH ~ 12 |
|---|---|---|---|---|
| Excitation $\lambda_{max}$ | 460 nm | 492–494 nm | 492–494 nm | 500 nm |
| $\epsilon \times 10^{-4}$ | <0.5 | ~5 | ~5 | ~8 |

TABLE 4-continued

| | pH ~ 2* | pH ~ 7 | pH ~ 9 | pH ~ 12 |
|---|---|---|---|---|
| Emission $\lambda_{max}$ | 503 nm | 511–513 nm | 511–513 nm | 520 nm |
| Relative fluorescence (%) | ~0 | >90 | 100 | <5 |

*Without $Al^{3+}$

Fluorescein complexon, except at acid pH, has a high molar extinction coefficient and a high fluorescence efficiency. When excited with visible light, fluorescein complexon exhibits an intense, visible, green fluorescence emission. The excitation and emission maxima are given listed in Table 4. Fluorescence emission intensity decreases sharply and linearly between pH 6.5 and 4.5. This is due to titration of the 3-hydroxyl group, which has a pK of 5.4. Fluorescence emission intensity again decreases above pH 9, in the range of about $10^{-9-10}$ mol $H^+$/l, due to titration of a residue and opening of the lactone ring at pKs of 10.5 and >12, respectively. Using white light excitation, pH-dependent fluorescence changes of $10^{-10}$ are easily measured. Higher sensitivities can be achieved by monitoring emission with a fluorometer or fluorescence spectrometer. Between 0.025–0.5 μg fluorescein complexon can be applied to a 100 mm$^2$ area detector having a thickness of 0.2 mm to form a suitable detector.

In other implementations, the indicator dye can be a colored dye having a visible optical absorbance. While a variety of dyes may be used in a detector, the high pK values of the dyes listed in Table 5 make them suitable for preparing a detector. Suitable dyes can be phthalic acid derivatives, such as o-cresolphthalein (pK 9.4; $\lambda_{max}$ 566 nm; molecular weight 346 g/mol) and phenolphthalein (pK~9.5; $\lambda_{max}$ 522 nm: molecular weight 318 g/mol), which have molar extinction coefficients near $3\times10^4$ are red in alkaline solution and change from colorless to red nearly linearly between pH 8.7 and 9.7, in the range of about $10^{-9}$ to $10^{-10}$ mol $H^+$/l. The dyes exhibit a large and distinctive color change at alkaline pH. The same is true for thymolphthalein (pK~9.9; $\lambda_{max}$ 592 nm), which is blue at highly alkaline pH and changes from colorless to blue between pH 8.9 and 10.9 in an essentially linear fashion between pH 9.4 and 10.4, in the range of about $10^{-9}$ to $10^{-10}$ mol $H^+$/l.

TABLE 5

| Indicator | Neutral color | Acid color | Basic color | pH range |
|---|---|---|---|---|
| o-Cresolphthalein | colorless | colorless | red | 8.2–9.8 |
| Phenolphthalein | colorless | colorless | red | 8.3–10 |
| Thymolphthalein | colorless | colorless | blue | 8.8–10.5 |

To provide a calculated absorbance of about 1 for a 0.2 mm thickness, about 1.5–3 μg (4.6–9.2 × $10^{-9}$ mol) colorimetric indicator applied to a 100 mm$^2$ area.

The analyte-sensing composition includes a buffer. The buffer can provide a stable pH within one pH unit of the pK of the indicator dye. The buffer can improve color stability of the detector. Buffer concentrations can be between 0.001 to 0.1 M, or 0.01 to 0.05 M. The ratio of buffer/indicator dye can be a molar ratio of between 20 and 200, such as between 40 and 100, or between 50 and 75, and more typically 50. Suitable buffers include amino acids, such as lysine and glycine, N,N-(bis-2-hydroxyethyl)glycine, 1,5,(4) dimethylimidazole, 2-amino-2-methyl-1,3,-propanediol, 2-amino-2-ethyl-1,3-propanediol, diethanolamine, ethanolamine, 2-(cyclohexylamino)ethane sulfonic acid or 2-amino-2-methyl-1-propanol. A borate buffer can be used in place of or in combination with an amino acid in certain applications. Suitable buffers and acceptors are listed in Table 6.

TABLE 6

| Buffer system | | pK |
|---|---|---|
| Acetic acid | | 4.76 |
| 2-(N-Morpholino)ethane sulphonic acid (MES) | | 6.09 |
| Tris(hydroxymethyl)aminomethane | | 8.08 |
| N,N-(bis-2-hydroxyethyl)glycine (BICINE) | | 8.26 |
| 2-amino-2-methyl-1,3-propanediol | | 8.79 |
| 2 amino-2-ethyl-1,3-propanediol | | 8.80 |
| Boric acid | | 9.14 |
| Glycine | $pK_2$ | 9.78 |
| Amino-2-methyl 1-propanol | | 9.7 |
| Lysine | $pK_2$ | 9.18 |
|  | $pK_3$ | 10.79 |
| Carbonic acid | $pK_2$ | 10.33 |
| Lysyl-lysine | $pK_2$ | 7.35 |
|  | $pK_3$ | 10.05 |
|  | $pK_4$ | 11.01 |
| Phosphoric acid | $pK_3$ | 12.38 |

Ion-free water can be used to manufacture the detector. Moreover, chelants such as ethylene diamine tetraacetic acid (EDTA), between $1 \times 10^{-4}$ and 0.001 M, can be included in the analyte-sensing composition to reduce or prevent interference with analyte detection that can be encountered when di- or trivalent cations are present. The manufacturing environment is further controlled by keeping all steps of manufacture free of volatile acid or base contaminants. Exposure to sunlight and ultraviolet light can also be avoided during manufacture.

Carbon dioxide reacts very rapidly with uncharged amino groups of primary and secondary aliphatic amines and amino acids releasing one mole $H^+$ per mole of carbon dioxide and creating a carbamino group in the reaction $RR'NH + CO_2 \Rightarrow RR'NCOO^- + H^+$, where each of R and R', independently, is H, straight or branched-chain alkyl, straight or branched-chain alkenyl, straight or branched-chain alkynyl, straight or branched-chain heteroalkyl, cycloalkyl, cycloheteroalkyl, or aryl. Each of R and R' is optionally substituted. When one of R or R' is H, the amine is a primary amine. Upon exposing the amine to carbon dioxide, the total dissolved carbon dioxide (dissolved gas+ carbonic acid) will essentially equal $pCO_2$ plus the concentration of $RR'NCOO^-$ where $pCO_2$ is the partial pressure of carbon dioxide. The detector can monitor the presence of carbon dioxide using this carbamino-forming reaction. For example, in order to differentiate between 20% and 25% carbon dioxide, the detector monitors a pH difference of 0.1 unit.

The potential advantages of utilizing the carbamino reaction to detect carbon dioxide include (a) carbon dioxide selectivity and (b) carbon dioxide sensitivity. The carbamino system has more that 1000-times the sensitivity than conventional, carbonic acid/bicarbonate systems using colorimetric indicators. Because of the high pK of carbamic acid, stable carbamino groups do not form below pH 7. However, when the pH is 2 units above the pK of the carbon dioxide acceptor amino group, more than 99% of the amino group occurs as RR'NH, the unionized carbamino group. Then $pH = pK_{carb} + \log[RR'NCOO^-]/[RR'NH]qpCO_2$, where $pK_{carb}$ is the pK of the carbonate reaction. Assuming a pH equal to 10 (100% carbon dioxide at 25° C.) qp is 0.033 and log qp is −1.48. With $pK_{carb} = 5.5$, $\log[RR'NCOO^-]/[RR'NH]$ will be about 6.6 and the ratio carbamino/amine will be about $10^6$. For 0.05% $CO_2$ at 10° C., qp is $1.55 \times 10^{-4}$, log qp is −3.8 and the ratio about 5 (i.e. about 83% carbamino). Accordingly the operating pH used in the detector is 10.

For the carbamino carbon dioxide assay to work accurately, a buffer system can be employed, using an amine, amino acid, a polyamino acid such as lysine, 2-amino-2-methyl 1-propanol, lysyl-lysine, polylysine, other polyamines, or combinations thereof. The buffer maintains the pH at preselected, set, alkaline values, and a concentration ranging from buffer/indicator ratios of 5 to −20, depending on specific application. Buffer/indicator ratios of 5–20 are preferred in order to ensure carbamate formation and provide stability.

The carbamino carbon dioxide assay also requires a carbon dioxide acceptor in the analyte-sensing composition. The carbon dioxide acceptor can be a primary or secondary aliphatic amine, amino acid, polyamino acid, or a combination thereof. The carbon dioxide acceptor reacts with carbon dioxide at alkaline pH to form carbamino acids. Concentrations of the carbamino acids depend on the nature of the sample being tested ($10^{-8}$ to $10^{-9}$ mol). The carbon dioxide acceptors, partially listed in Table 6 includes tris (hydroxymethyl)aminomethane, lysyl-lysine, 2-amino-2-methyl-1,3-propanediol, 2 amino-2-ethyl-1,3-propanediol and other primary or secondary amines with pKs at least one pH unit above pH 7 and at least one pH unit below the pK of the indicator.

Indicators capable of functioning at high pH are summarized in Table 7 using a lysine buffer, which respond in the range of about $10^{-9}$ to $10^{-10}$ mol $H^+/l$, or the range of $10^{-9}$ to $10^{-10}$ mol/l carbon dioxide as $-NH-COO^-$.

TABLE 7

| Indicator | Set pH | Set color | Change |
|---|---|---|---|
| Fluorescein complexon | ~11 | Slight fluorescence | ↑fluorescence |
| Phenolphthalein | ~10 | red | ↓color |
| Thymolphthalein | ~10 | blue | ↓color |

Under the test conditions, the fluorescence of fluorescein complexon is initially near a minimum and the colors of the colorimetric indicators at a maximal. With introduction of carbon dioxide, the pH of an aqueous solution decreases because a proton is released for each molecule of carbon dioxide encountered. As result, the fluorescence of fluorescein complexon increases and color indicator dyes lose color. Increasing $pCO_2$ the amount of carbamate rises until the system becomes acidic enough to convert RR'NH to $RR'NH_2^+$, which cannot form $RR'NCOO^-$. The performance of the detector can depend on the buffer/indicator ratio.

Volatile carboxylic acids can be detected as an analyte if the indicators used for the assays of carbamino carbon dioxide are used for the detection of the volatile carboxylic acids listed in Table 1, and an additional carbon dioxide acceptor is used. Three approaches to a detector are presented in Table 8 using fluorescein complexon. Because of its biphasic pH-fluorescence properties, as well as the fluorescence of its complex with $Al^{3+}$, present at a level of at most $10^{-6}$ M $Al^{3+}$ in acetate buffer. The fluorescence of fluorescein complexon increases sharply between pH 5 and pH 2. See D. F. H. Wallach and T. L. Steck, 1963, loc. cit. The $Al^{3+}$ complex can increase green fluorescence intensity, making it easier to discern a change in ordinary light than a decrease. Other high pK buffers, such as boric acid, could be used in certain implementations.

TABLE 8

| | Buffer | Set pH | Set fluorescence | Change with acid |
|---|---|---|---|---|
| Fluorescein complexon | MES | ~6 | High | ↓ |
| Fluorescein complexon/$Al^{3+}$ | Acetic acid | ~5 | Low | ↑ |
| Fluorescein complexon | Phosphoric acid | ~11 | Slight | ↑ |

Another analyte, a volatile amine, can also be monitored with the detector. Specifically, the indicators used for the carbamino assay can also be used for the detection of methylamine, trimethylamine, cadaverine and putrescine, all with pKs near 10 or above, using a lower set pH for the detector. A variety of indicators for these detectors is shown in Table 9. A different buffer system (a BICINE system) and eliminating the carbon dioxide acceptor amines facilitates the volatile amine detection. BICINE is given as buffer in this example because it is suitable for fluorescein complexon, as well as phenolphthalein and thymolphthalein. Buffers with somewhat lower pKs can be suitable to form the colorimetric detector.

TABLE 9

| Indicator | Set pH | Set color | Change |
|---|---|---|---|
| Fluorescein complexon | ~8.5 | High fluorescence | ↓fluorescence |
| Phenolphthalein | ≦8.5 | colorless | colorless→red |
| Thymolphthalein | ≦8.5 | colorless | colorless→blue |

The fluorescence system of Table 6 can be further modified for the detection of ammonia. The modification is needed to detect ammonia due, in part, to the molecule's relatively low pK of 9.25, and running into the fluorescence-pH maximum of free fluorescein complexon. In acetate buffer Table 7, fluorescein complexon will increase in fluorescence upon addition of ammonia. The BICINE buffer would then be used with the colorimetric dyes. Each of these approaches can be useful to formulate a detector for monitoring a hygiene product such as a diaper.

TABLE 7

| Indicator | Buffer | Set pH | Set color | Change |
|---|---|---|---|---|
| Fluorescein complexon | Acetic acid | ~5 | Low fluorescence | ↑fluorescence |
| Phenolphthalein | BICINE | ≦8.5 | colorless | colorless→red |
| Thymolphthalein | BICINE | ≦8.5 | colorless | colorless→blue |

The emission change that the analyte-sensing composition produces, when the fluorescence of fluorescein complexon is being detected, can be seen visually in normal light. Light sources with an ultraviolet component such as "plant lights," non-UV shielded halogen lights, and black lights can lead to undesirable photobleaching of the dye with time. Intense, white beams, such as can be obtained with many of the inexpensive, UV-shielded halogen lights (e.g. 20 W, 12 v), focussed on the detector can easily be used as a light source, even without simple filters. Alternatively, blue light-emitting diodes or white light emitting diodes can be used as lights sources. The working concentration of dye can be in the range of $1 \times 10^{-11}$ M to $5 \times 10^{-8}$ M, or $2 \times 10^{-9}$ M, roughly corresponding to $4 \times 10^{-11}$ for a 20 μl device. For more complicated purposes, many devices, including fluorometers, one and two channel spectrofluorometers, fiber optic devices and laser devices can be used to monitor the emission.

Visual detection of color changes can be relied on for many consumer uses, such as in packages and bandages. As with the emissive detectors, instrumental detection can be suitable for precise and highly sensitive measurements relating to automation, supermarkets or laboratories.

EXAMPLES

The following examples are provided.

With the exception of the fluorescence assays of volatile acids at acidic pH in the detectors, the intrinsic sensitivity of the fluorescence system of this detector is on the order of pH changes about $10^{-10}$ mol/L. With a detector volume of 20 μl, this corresponds to about $2 \times 10^{-15}$ mol for volatile acids and bases above pH about 10. The sensitivity depends on the buffer/indicator ratio. Because of the very low concentration of dye in the sensing composition, fluorescein complexon itself does not exert a noticeable buffer effect. However, at the buffer/indicator ratios of 10–20 desired for stability, sensitivity is reduced to about of $2 \times 10^{-14}$ mol. The sensitivity per mole of carbon dioxide around pH 10 is similar. Because of the high instrumental sensitivity of fluorescence, much higher overall sensitivities can be attainable.

The intrinsic sensitivity of the colorimetric systems falls also in the order of changes $10^{-10}$ mol/L made. However, because the colorimetric indicators are present at a concentration of greater than $10^{-9}$ mol/L, the real sensitivity is set by the indicator concentration. With a detector volume in the order of 20 μl, this corresponds to a sample volume of about $10^{-14}$ mol. At the buffer/indicator ratios of 10–20, which is desired for stability, sensitivity is reduced to about of $2 \times 10^{-13}$ mol. The carbon dioxide sensitivity at pH greater than 10 is similar.

In the absence of permeation barriers or permeation modulation layers, the detectors can respond to the analytes in Table 1 within a second. Consider, for example, shifting the environment of a detector system from $pCO_2$ of 0 to $pCO_2$ of 1 atmosphere. This delivers about 0.03 mol $H^+$/l to the system at alkaline pH, or $6 \times 10^{-7}$ mol per 20 $mm^3$ detector within the time required to change the atmosphere. If the detector equilibrated at $pCO_2$ of 1 atmosphere and was shifted to $pCO_2$ of 0, about 0.03 mol $H^+$/l would be extracted from the system at alkaline pH, or $6 \times 10^{-7}$ mol per 20 $mm^3$ detector within the time needed to make the atmosphere change. An internal configuration, as shown in FIG. 2, can be used when very rapid responses are desired or permitted.

The detector can be used in a label configuration when the detector is placed as a label on food wrap. The food wrap serves as a permeation modulator, as shown in FIG. 3. If a detector with a 100 mm² permeation area is placed on a 0.01 mm thick low density polyethylene cling wrap and a change in analyte concentration, due to a metabolic process, of $pCO_2$ from 0 to 0.001 atmospheres takes place, this would deliver $3\times10^{-5}$ mol $H^+$/l to the detector at alkaline pH, or $6\times10^{-9}$ mol per 20 mm³ detector. The detector registers a response after 100 seconds for a fluorescence-based detector and 1000 seconds for a colorimetric-based detector, assuming a buffer/indicator ratio near 10. An analyte shift to 0.001 atmospheres is calculated to be detectable by the fluorescence-based detector with an equally thick permeability barrier of PVC is 4 times faster. With $1.5\times10^{-4}$ mol $H^+$/l delivered, the colorimetric response occurs at 1800 seconds. The responses to higher molecular weight analytes are much slower. For example, response times of 4–8 hours for 0.1 M acetic and lactic acids, respectively, have been observed.

Modified atmosphere packaging can use between 1 and 0.2 atmospheres of carbon dioxide depending on the product. Desired carbon dioxide concentrations are obtained by, for example, flushing the packages with appropriate gas mixtures, or, alternatively, by introducing solid carbon dioxide-producing mixtures such as citric acid/sodium bicarbonate mixtures into the packages. Modified atmosphere packages are usually sealed with a carbon dioxide-impermeable, transparent plastic layer. To monitor the carbon dioxide content of packages, and possible leaks, the detector can be located inside the package in a position where it can be viewed. For example, the detector can be located with the external surface (FIG. 2) adhered to the inside of the transparent cover. Since there are no permeability barriers, a 1% leak or more of the internal carbon dioxide content should be detectable by either the fluorescence- or the colorimetric-based detector within seconds.

In other applications, meats are often packed under vacuum to preserve freshness by reducing $pO_2$ in order to avoid degradative oxidative processes. Nevertheless, some oxidative metabolism continues yielding carbon dioxide. The production of carbon dioxide in vacuum packages using the detectors can be readily monitored.

The following examples illustrate use of the detector to create a time/$CO_2$ detector that discriminates between short and more extended changes in $pCO_2$ within carbon dioxide-containing packages. Fluorescence or carbamino detector systems are used and monitoring time is initiated after setting the $pCO_2$ inside the package. The $pCO_2$ levels can be well below those used for modified atmospheres. For this purpose, the detector would be charged with carbon dioxide prior to application to, for example, a food package. This can be done in a number of ways, for example, by equilibration with carbon dioxide gas to saturate the carbon dioxide-acceptor amine, followed by applying a sealing backing which stays in place until the sensor is applied to the package.

The following variations are available to adjust the duration time for time/time temperature applications from 5 to greater than $2.5\times10^6$ seconds. The response time of the detector without a permeation modulator barrier can be too fast for time measurements. Even with a food wrap permeation modulator, the maximum time can be too short, on the order of 5–500 seconds, for many applications. Reducing the permeation area from, for example, 1 cm×1 cm, (1 cm²) to, for example, 0.1×0.1 cm (0.01 cm²), by using a perforated hydrophobic layer, can reduce the rate of by a factor of 100. Increasing the barrier membrane thickness from 0.001 mm to 1 mm can increase the time required to achieve a fluorescence/color change by a factor of 2000. Increasing the buffer/indicator ratio to 100, can increase the time required to achieve a fluorescence color change by 10. Various combinations of the above-mentioned variations can result in analysis times ranging from $2.5\times10^6$ seconds to greater than 29 days.

The detectors can have two important temperature-sensitive components, including the exothermic character of the carbamino formation and a positive activation energy which tends to increase the rate of reaction as temperature is raised. If the detector is calibrated to change near 29 days at 25° C., it could change about 5 days earlier at 40° C.

Ammonia

Due to the breakdown of urea by coliform bacteria, ammonia can be present at high e concentrations in adult and baby diaper fluid to cause skin irritation. A typical urine urea concentration is 0.3 M/l. The action of bacterial urease yields two molecules of ammonia and one of molecule of carbon dioxide. Bacterial conversion of 0.01% of the urea, for example, yields about $3\times10^{-5}$ mol ammonia. The outer layers of diapers are commonly constructed of plastic that allows rapid permeation of water vapor and ammonia. A detector with an inner surface adhered directly to the outer diaper surface can signal for diaper change upon detection of ammonia.

Amines

Shrimp, as well as other seafood, contain substantial amounts of muscle trimethylamine which is released post mortem. Trimethylamine permeates membranes such as polyethylene and polyvinyl chloride. After 8 hours, the gas phase within the package equilibrated with $10^{-4}$ M trimethylamine. Since the pK of trimethylamine is near 9.9 (at 20° C.), it can form salt complexes with carbon dioxide in a controlled atmosphere package. This can result in a decrease of $pCO_2$ that can be monitored with a detector that is not due to a package leak.

Juice Packages

Fruit juices, which are often unpasteurized, can be packaged in paper laminate containers that prevent external contamination by microorganisms and also avoid light-induced degradation. There can be appreciable yeast or microbial contamination in the juice, leading to the production of carbon dioxide and acetic acid. The carbon dioxide and acetic acid production can be monitored by incorporation of the detector into the package walls of the juice container, or in a cap.

Blood, Internal Body Fluids

With the appropriate buffer systems, for example, lysine for detecting carbon dioxide and BICINE for detecting ammonia, the detector can be applied to determine carbon dioxide or ammonia concentrations in internal body fluids and gases. For example, a specialized test tube can have a detector attached to the wall or bottom with a 0.001 cm, 100 mm² low-density polyethylene membrane covering the inner surface and containing on the order of $2\times10^{-9}$ mol indicator, $2\times10^{-8}$ mol acceptor amine and $1\times10^{-8}$ mol buffer. A sample of blood/plasma near pH 7.4 ($pCO_2$ 35–40 mm Hg) is introduced into the tube, avoiding contamination with the atmosphere, covering the exposed detector surface. The blood sample contains about $5\times10^{-4}$ (0.0005) mol $H^+$/l. About $5\times10^{-8}$ mol $H^+$ is delivered to the detector compartment within one second. Without the membrane, the change is more rapid but the system might be unstable. The sensor can be similarly incorporated into the wall of a flow-through tube.

Bandages

In another example, phagocytic cells, which can populate an infected wound, generate about $10^{-10}$ mol $CO_2$ per sec.cm$^2$ (calculated from P. G. Munder, et al. FEBS Letters, 15:191–196 (1971) and M. Jensen, et al. Experimental Cell Research, 84:271–281 (1974). A detector having the sensitivity given in the previous example can be placed on a surface wound in the manner of a bandage and would indicate phagocytic activity within less than 1 second.

Detector Kits

Individual detectors are composed with predetermined reaction times by modifying the variables discussed above, for example, by modifying the permeation modulator. The outer layers of the detectors are provided with self-adherent strips. The detectors can be prepared as strips, cut and packaged in gas impermeable film or foil. The detectors can then be applied in the home, for example, to monitor unwrapped food or opened packages, or elsewhere to monitor carbon dioxide, ammonia, volatile carboxylic acids and volatile amines. Detector response times can be preselected to detect changes over a 1 day, 1 week or 1 month period.

Flow-through Detector

The detector can be configured to be a portion of a flow-through tube, as shown in FIG. 5. Instrumental monitoring of the detector permits continuous readings to be taken, and analyte concentration changes be monitored over time. No permeability modulator is involved, permitting the detector to respond rapidly to sample changes. For clinical purposes, a small volume (less than 0.2 mL) of a gas or fluid can be injected through a typical fitting, such as a Luer fitting, displacing residual gas/liquid volume.

Other embodiments are within the scope of the following claims.

What is claimed is:

1. A method of detecting an analyte comprising:

contacting a detector with a food product, body fluid or tissue, the detector including:

a carrier;

an analyte-sensing composition including an indicator dye, a buffer, and an osmotic control agent, the analyte-sensing composition being contained by the carrier;

a hydrophobic barrier on one surface of the carrier, and the buffer and indicator dye are present in a molar ratio of between 20 and 200 the hydrophobic barrier being arranged to contact the food product, body fluid or tissue, and an outer barrier covering a surface of the carrier opposite the hydrophobic barrier; and monitoring the detector for a change in visible color intensity or emission intensity from the indicator dye which indicates the presence of the analyte.

2. The method of claim 1, wherein monitoring includes detecting the change with an instrument.

3. The method of claim 1, wherein the analyte includes carbon dioxide, a volatile amine or a volatile carboxylic acid.

4. The method of claim 1, wherein the detector is a portion of a food package or a hygiene product.

5. The method of claim 1, wherein the presence of the analyte changes the pH within the carrier.

6. The method of claim 1, further comprising removing the detector from a sealed package prior to contacting the food product, body fluid or tissue.

* * * * *